United States Patent
Lupton et al.

(10) Patent No.: US 10,538,444 B2
(45) Date of Patent: Jan. 21, 2020

(54) DIGESTION OF ELEMENTAL SULFUR IN BIOREACTOR DURING BIOLOGICAL OXIDATION OF SULFIDE IN WASTEWATER AND GROUNDWATER

(71) Applicant: UOP LLC, Des Plaines, IL (US)

(72) Inventors: F. Stephen Lupton, Evanston, IL (US); Rachel E. Hanson, Denver, CO (US); William G. Sheridan, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 39 days.

(21) Appl. No.: 15/833,229

(22) Filed: Dec. 6, 2017

(65) Prior Publication Data

US 2018/0170781 A1     Jun. 21, 2018

Related U.S. Application Data

(60) Provisional application No. 62/437,613, filed on Dec. 21, 2016.

(51) Int. Cl.

| | |
|---|---|
| *C02F 3/34* | (2006.01) |
| *C02F 11/06* | (2006.01) |
| *C02F 11/02* | (2006.01) |
| *C02F 3/12* | (2006.01) |
| *C02F 3/10* | (2006.01) |
| *C02F 3/30* | (2006.01) |
| *C12M 1/00* | (2006.01) |
| *C01B 17/16* | (2006.01) |

(Continued)

(52) U.S. Cl.
CPC ............. *C02F 3/345* (2013.01); *C02F 3/105* (2013.01); *C02F 3/121* (2013.01); *C02F 11/02* (2013.01); *C02F 11/06* (2013.01); *C12M 23/34* (2013.01); *C01B 17/16* (2013.01); *C01B 17/69* (2013.01); *C02F 2101/101* (2013.01); *C02F 2103/06* (2013.01); *C02F 2103/34* (2013.01)

(58) Field of Classification Search
CPC .... C02F 3/30; C02F 3/2806; C02F 2101/101; C02F 3/06; C02F 3/10; C02F 3/34; C02F 3/345; C02F 3/105; C02F 3/108; C02F 3/121; C02F 11/02; C02F 11/06; B01D 53/84; B01D 2257/30; B01D 2257/304
USPC ................ 210/605, 617, 610, 615, 616, 620
See application file for complete search history.

(56) References Cited

U.S. PATENT DOCUMENTS

| | | | |
|---|---|---|---|
| 4,760,027 A * | 7/1988 | Sublette | ................. B01D 53/84 |
| | | | 435/266 |
| 5,449,460 A | 9/1995 | Buisman | |
| 5,637,220 A * | 6/1997 | Buisman | ................. C01B 17/05 |
| | | | 210/605 |

FOREIGN PATENT DOCUMENTS

RU     2010113444 A     10/2011

OTHER PUBLICATIONS

International Search Report from corresponding PCT application No. PCT/US2017/066010, dated Mar. 6, 2018.

(Continued)

*Primary Examiner* — Claire A Norris (57) ABSTRACT

A method is presented for biological removal of contaminants like sulfide from ground waters and industrial waters. A fixed film compartmentalized bioreactor or bioreactors are used to convert sulfide to elemental sulfur and the subsequent conversion of the elemental sulfur to sulfates. The present invention uses a packed bed bioreactor configuration that uses packing material to maximize the concentration of sulfide oxidizing bacteria.

20 Claims, 3 Drawing Sheets

(51) Int. Cl.
  *C02F 103/06* (2006.01)
  *C02F 101/10* (2006.01)
  *C02F 103/34* (2006.01)
  *C01B 17/69* (2006.01)

(56) References Cited

OTHER PUBLICATIONS

Written Opinion from corresponding PCT application No. PCT/US2017/066010, dated Mar. 1, 2018.
International Preliminary Report on Patentability from corresponding PCT application No. PCT/US2017/066010, dated Jun. 25, 2019.
Buisman, Gees J.N., et al., Optimization of Sulphur Production in a Biotechnological Sulphide-Removing Reactor, Biotechnology and Bioengineering, 1990, vol. 35, pp. 50-56. (Abstract Only).

* cited by examiner

DIGESTION OF ELEMENTAL SULFUR IN BIOREACTOR DURING BIOLOGICAL OXIDATION OF SULFIDE IN WASTEWATER AND GROUNDWATER

CROSS-REFERENCE TO RELATED APPLICATION

This application claims priority from Provisional Application No. 62/437,613 filed Dec. 21, 2016, the contents of which cited application are hereby incorporated by reference in its entirety.

BACKGROUND

The present invention relates generally to method for the removal of pollutants from water. More specifically, the present invention relates to methods for biological conversion of hydrogen sulfide in solution to sulfate ion in high salinity ground waters and industrial wastewaters.

Environment-conscious industries are continuously laboring toward the goal of removing pollutants from contaminated water to make the water safe at both the ground level and the consumer level. Government-regulated agencies establish limits for many common industrial pollutants. These limits tend to become stricter as pollutant reduction and removal technology proves effective at accomplishing previously-established requirements. Consequently, both ground and consumer level water continue to improve in terms of both purity and safety.

Among the methods employed to reduce and remove pollutants, bioremediation constitutes an effective and desirable technology. In a broad sense, bioremediation includes the use of microorganisms that digest pollutants as a source of food, including nitrogen and carbon compounds. Bacterial metabolism can convert the pollutants to metabolites having a simple chemical structure to carbon dioxide and water in an aerobic process, or to methane in an anaerobic process. In any respect, the metabolites produced by bacteria typically have no adverse environmental effects.

The use of large volumes of water in hydraulic fracturing or "fracking," a technique to enhance the recovery of natural gas from organic containing shale deposits, has led to restrictions on use of fresh water reserves both above ground and from potable ground waters. The use of non-potable deep ground water brines for fracking does not put a strain on these fresh water reserves, but it does introduce new challenges, especially with regards to high levels of hydrogen sulfide present in brines. Several chemical processes have been developed, including chemical oxidation or stripping/adsorption techniques for sulfide removal from waste water, but they tend to be relatively expensive and require an undesirably large amount of time, machinery and high operational costs. Sludge disposal is one of major operating costs of biological treatment systems. The use of sulfur oxidizing bacteria that produces elemental sulfur in a suspended growth system produces large amounts of solids that contribute to sludge formation of both elemental sulfur solids and biological solids.

The oxidation of sulfides by the chemolithotrophic bacteria in a bioreactor to remove sulfide requires oxygen. The oxygen is generally provided by sparging air directly to the bioreactor. However, air sparging can result in extensive stripping of hydrogen sulfide out of the water phase before the bacteria are biochemically oxidize the sulfide to either elemental sulfur or soluble sulfate. Additionally, the stripped sulfide requires extensive scrubbing from the vent gas. Therefore, in an attempt to reduce stripping of sulfide during biological treatment of high sulfide groundwater or wastewater, a low aeration is utilized. But low aeration favors biological conversion of sulfide to insoluble elemental sulfur rather than sulfide due to low dissolved oxygen levels in bioreactor. The formation of elemental sulfur is problematic as it requires separation and solids handling as its disposal. The build-up of elemental sulfur can lead to plugging problems in the bioreactor resulting in poor sulfide removal and a greater proportion of sulfide in the off-gas stream.

Therefore, there is a need for an improved method and apparatus for removing sulfides and their conversion in a cost and time efficient manner. It is also desirable to provide such methods and systems that can replace some conventional chemical processes for removal of sulfides with improved biological processes that produce less sludge and thereby reduce the requisite time, machinery, and operational costs for performing the processes.

SUMMARY

An embodiment of the present invention is a process for biological conversion of hydrogen sulfide in a solution to sulfate ion in a feed water stream using a fixed film compartmentalized bioreactors, comprising passing the feed water stream through a first stage of the fixed film compartmentalized bioreactor operating under low aeration conditions. The hydrogen sulfide is oxidized to elemental sulfur. Only a small amount of hydrogen sulfide from the first stage of the bioreactor is stripped. Much elemental sulfur is entrapped on the packing material in this section of the bioreactor. Some of the elemental sulfur is passed to a second stage of the fixed film compartmentalized bioreactor operating under high aeration and pH control. The elemental sulfur is oxidized to sulfate ion. A purified water stream is removed from the second stage comprising sulfides in the range of about 0.1 mg/L to about 0.5 mg/L sulfides from said bioreactor. An effective quantity of autotrophic obligate chemolithotrophic bacteria is immobilized on a highly porous foam packing material with high surface area within said bioreactor. Two bioreactors may be operated in parallel. One bioreactor may treat the sulfide containing water while the other may be operated in a batch mode. In the bioreactor that is being operated in batch mode, the elemental sulfur that is entrapped in the bioreactor packing may be further oxidized to sulfate ion.

The present invention seeks to provide a process for removing sulfides from a water stream in a bioreactor in a cost and time efficient manner. A benefit of the present invention is that the process of biological oxidation of sulfide to sulfate using a compartmentalized reactor with a highly porous packing material with high surface area negates the need for any handling of wet elemental sulfur suspensions and greatly reduces materials handling issues. The process advantageously avoids stripping, solid separation and disposal issues. These and other features, aspects, and advantages of the present invention will become better understood upon consideration of the following detailed description, drawings and appended claims.

DETAILED DESCRIPTION

The microbial oxidation of reduced sulfur species by the use of bacteria, especially photosynthetic bacteria, to oxidize sulfide to elemental sulfur in a suspended growth mode is known. Bacteria have developed enzymes which are orders of magnitude more efficient than abiotic oxidation of sulfides by molecular oxygen. The present invention provides a method of using non-photosynthetic chemolithotrophic sulfur oxidizing bacteria that can oxidize sulfide to soluble sulfate rather than elemental sulfur. The bacterium that oxidizes sulfides to elemental sulfur often produces granules of sulfur so that sulfur is retained in the biomass.

Figure 3:
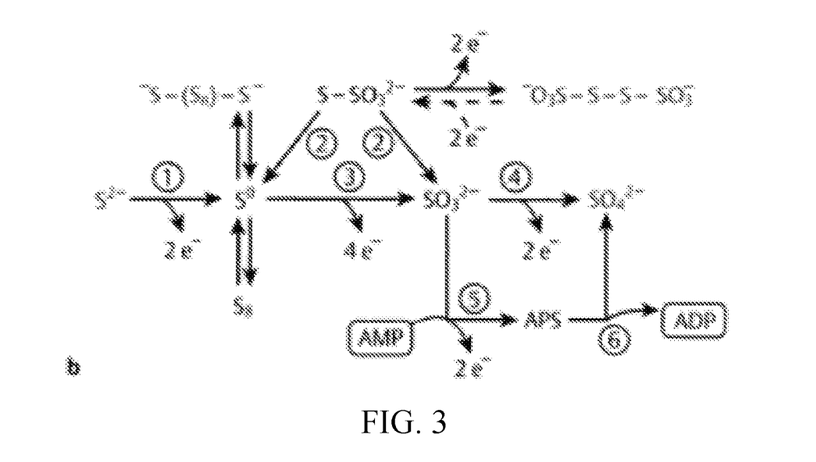
FIG. 3 is an illustration of a biochemical process involved in the embodiments of the present invention.
Figure 4:
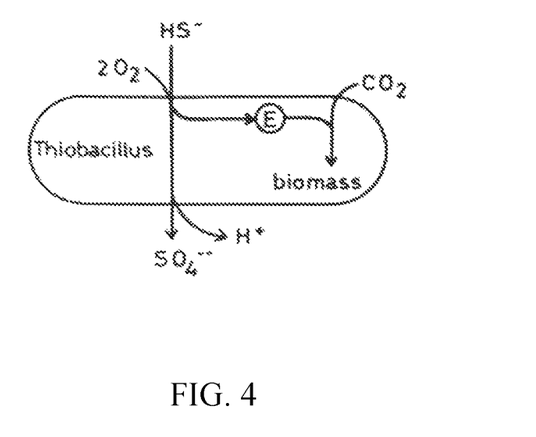
FIG. 4 is an illustration of another biochemical process involved in the embodiments of the present invention.

The autotrophic obligate chemolithotrophic bacteria that are used in the present invention are a group of bacteria that gain metabolic energy from the oxidization of reduced sulfur compounds instead of gaining energy from the oxidation of organic compounds, unlike most other organisms. They grow by fixing carbon dioxide into organic compounds just like photosynthetic organisms. They use chemical energy from sulfide oxidation rather than light energy to do this biochemical step. The biochemical processes involved in the mechanism are illustrated in FIGS. 3 and 4.

The chemolithotrophic bacteria used in the present invention are obligatory halotolerant and acidophilic. The bacteria may be found in marine or saline environments with salt concentration in excess of 1% total salinity. The optimal area to select the bacteria of the present invention is at the water/sediment interface, where the bacteria have access to both sulfide and oxygen.

The autotrophic obligate chemolithotrophic bacteria used in the present invention may be selected from the following species *Acidithiobacillus ferrooxidans, Thermithiobacillus tepidarius, Sulfurimonas denitrificans, Desulfocapsa sulfoexigens*, and some species of *Thiobacillus, Halothiobacillus, Acidiphilium, Thiomicrospira, Sulfolobus, Acidianus, Sulfurisphaera*, and *Sulfurococcus*. The chemolithotrophic sulfur oxidizing bacteria of the present invention can fully and efficiently oxidize sulfides to soluble sulfates.

The present invention provides a high performance bioreactor system that can be used to remove organics and sulfides from both gas and water streams using a proprietary bio-support and reactor design. The bioreactor system may be used to remove sulfide from sewer vent gas and organics formed during treatment of metal containing mining wastes. The bioreactor of the present invention is robust and provides cost effective solution for removal of sulfide from polluted water.

The present invention uses a packed bed bioreactor configuration that uses two different packing materials. The packing used may be dual or mixed media packing. The packing used according to the present invention allows the buildup of high concentrations of obligatory halotolerant acidophilic, chemolithotrophic bacteria in the bioreactor to develop in microbial biofilms. The chemolithotrophic bacteria may colonize in the dual packing material in the fixed film bioreactor to high concentration of about 10,000 mg/L of fixed biomass. The packing used in the bioreactor also minimizes plugging and enables to maximize the contact between the sulfide and bacteria. The mixed media packing may be a mixture of polyurethane foam and plastic ball rings.

The oxidation of sulfide to elemental sulfur results in formation of alkaline conditions:

Alkaline conditions in the saline groundwaters results in scaling due to formation of calcium salts. The oxidation of sulfide by the chemolithotrophic sulfur oxidizing bacteria on the other hand produces acidic conditions which helps prevent the scaling problem in the highly saline groundwaters.

The present invention provides a method to immobilize the bacteria in highly porous support matrix that prevents loss of bacteria and also reduces the solids leaving the bioreactor. The prevention of scaling problems allows the water to be used directly from the bioreactor as make-up water for fracking without any additional post-treatments like filtration. The oxygen is usually provided by air sparging to the bioreactor. Traditionally, hydrogen sulfide is first oxidized primarily to elemental sulfur and subsequently oxidized to sulfate in another bioreactor system. Commercial experience with this approach has highlighted a number of significant problems, including the need to transfer wet elemental suspensions and slurries between bioreactors. The nature of wet sulfur suspensions is the sticky nature of these solids, which results in significant fouling of pipes and pumps. The present invention is a significant improvement upon traditional process as it utilizes a compartmentalized reactor with a highly porous packing material with high surface area. A single bioreactor or multiple bioreactors operated in parallel may be used to conduct both hydrogen sulfide oxidation to sulfur and sulfur oxidation to sulfate due to the containment of sulfur within a single reactor by trapping the sulfur from the oxidation of hydrogen sulfide onto the porous packing and subsequently converting the adsorbed sulfur to sulfate. This negates the need for any handling of wet elemental sulfur suspensions and greatly reduces materials handling issues. This invention takes advantage of the sticky nature of wet elemental sulfur to deposit on surfaces in capturing the sulfur on the high porosity foam and trapping it for subsequent oxidation to sulfate by switching the bioreactor between low and high aeration conditions and by control of pH within the bioreactor. The present invention provides beneficially a design of a compartmentalized bioreactor with a highly porous packing material with high surface area to conduct both hydrogen sulfide oxidation to sulfur and sulfur oxidation to sulfate within a single reactor by trapping the sulfur from the oxidation of hydrogen sulfide onto the porous packing and subsequently converting the adsorbed sulfur to sulfate by altering the conditions of the bioreactor.

Figure 1:
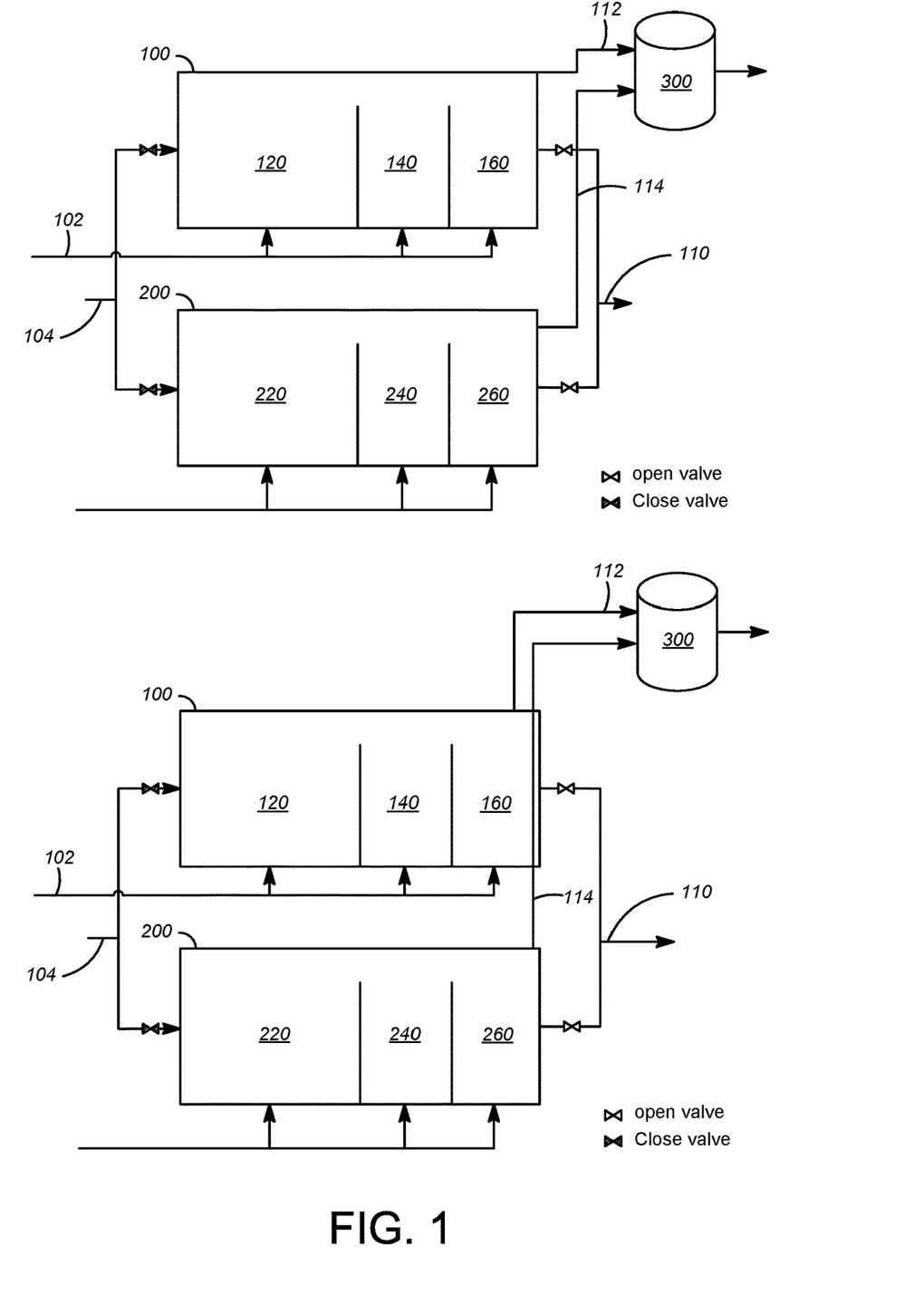
FIG. 1 is a schematic for the process of an embodiment of the present invention operated in mode A and mode B.

A general understanding of the apparatus and process for that biological conversion of hydrogen sulfide in a solution to sulfate ion can be obtained by reference to FIG. 1. FIG. 1 has been simplified by the deletion of a large number of apparatuses customarily employed in a process of this nature, such as vessel internals, temperature and pressure controls systems, flow control valves, recycle pumps, etc. which are not specifically required to illustrate the performance of the present invention. FIG. 1 shows three chambers of the bioreactor as a representation, but the process of the present invention is not limited to three chambers. Furthermore, the illustration of the process of this present invention in the embodiment of a specific drawing is not intended to limit the present invention to specific embodiments set out herein.

This process of the present invention can be practiced in a modular bioreactor configuration. The modular bioreactor configuration may include two compartmentalized bioreactors and may be operated in parallel. Each bioreactor may include three chambers. The first chamber may occupy 50% of the total reactor volume. The last two chambers of each bioreactor may occupy 25% of the total bioreactor volume each. The first immobilized compartmentalized bioreactors (ICB) 100 comprises a first chamber 120, a second chamber 140 and a third chamber 160 and the second immobilized compartmentalized bioreactors (ICB) 200 comprises a first chamber 220, a second chamber 240 and a third chamber 260. An effective quantity of autotrophic obligate chemolithotrophic bacteria is immobilized on a highly porous foam packing material with high surface area within the bioreactor. The packing material contains about 4,000 mg/L to about 12,000 mg/L of fixed biomass.

The compartmentalized bioreactors include a first inlet in line 104 for receiving the feed, a second inlet 102 for receiving air and an outlet in line 110 for releasing the effluent. The feed to the bioreactor may be an aqueous stream containing sulfides. Typical feeds include briny groundwaters, fracking wastewaters, sulfidic caustic wastewaters, sour waters from refining and petrochemical processing, sulfidic sewer water, and sour water generated by anaerobic digesters or mixtures thereof. The feed water stream may comprise a salt concentration of more than 1% total salinity. The concentration of sulfide in the aqueous feed to the bioreactor may be about 1 mg/L to about 2500 mg/L and preferably in the range of about 10 mg/L to about 1,600 mg/L and more preferably in the range of 100 mg/L to 150 mg/L. The sulfides may be present in the feed as hydrogen sulfide or metallic sulfides such as sodium sulfide or iron sulfides. There may be little or no dissolved oxygen in the aqueous feed to the bioreactors. The chemolithotrophic bacteria may be supported on a substrate housed inside the chambers in a fixed bed and situated to contact with the feed flowing there through. The autotrophic obligate chemolithtrophic bacteria are immobilized on a packing material within the bioreactors. The term "fixed bed" signifies that the biologically active components and the bacteria supported thereon are substantially stationary as the feed flows through the bioreactor. The biologically active components are primarily a porous substrate.

The feed water stream comprising sulfides in line 104 is passed through the first stage of the fixed film compartmentalized bioreactor 100 operating under low aeration conditions. The feed water stream is passed through the immobilized autotrophic obligate chemolithotrophic bacteria. The amount of air in the first stage may be about 0.1 scfm air/m$^2$ to about 1.0 scfm air/m$^2$ bioreactor surface area preferably of about 0.2 to 0.8 scfm air/m$^2$ bioreactor surface area and more preferably of about 0.3 to 0.5 scfm air/m$^2$ bioreactor surface area. The pH of the first stage may be in the range of about pH 2 to about pH 9. The hydrogen sulfide is oxidized to elemental sulfur in the first stage of the compartmentalized bioreactor. The elemental sulfur is trapped in the high porosity foam packing in the first stage. The elemental sulfur formed may either stick to the bioreactor packing media or flow out of the leading bioreactor into a following bioreactor with high aeration to complete the oxidation of elemental sulfur to hydrogen sulfate.

A majority of sulfides in the feed water stream are oxidized by the chemolithotrophic sulfur oxidizing bacteria. The sulfide containing feed is allowed to flow upflow through the packed bed of the bioreactor. The hydrogen sulfide is stripped from the first stage in lines 112 and 114 of the bioreactors. The stripped sulfide may be oxidized to sulfuric acid in a trickling bio-filter 300 or bio-filter type or with a sulfide adsorbent or oxidant. The hydrogen sulfide stripped is passed from the first stage to the trickling filter or a bio-filter to convert sulfide to sulfate ion (not shown). The ratio of air to sulfide in the trickling bio-filter 300 may be about 0.5 liters of air/mg of sulfide to about 4 liters of air/mg of sulfide.

The elemental sulfur is passed to the second stage of the fixed film compartmentalized bioreactors operating under high aeration conditions and controlled pH. The last two chambers of each of compartmentalized bioreactors may be always at high aeration to promote oxidation of elemental sulfur that escapes adsorption onto the packed bed trap to sulfuric acid before the residual elemental sulfur leaves the bioreactor with the flow of water. The amount of air in the second stage is about 1.0 scfm air/m$^2$ to about 5.0 scfm air/m$^2$ bioreactor surface area, preferably of about 1.5 to 3.5 scfm air/m$^2$ bioreactor surface area and more preferably of about 2 to 2.5 scfm air/m$^2$ bioreactor surface area. The pH in the second stage may be in the range of about pH 2 to about pH 9. The pH in the second stage may be controlled in the range of about pH 2 to about pH 9 by addition of a base such as sodium hydroxide or sodium carbonate. The fixed film compartmentalized bioreactors can operate at any suitable temperature, and typically operates at a temperature in the range of about 10° C. to about 65° C., preferably can operate at a temperature in the range of about 15° C. to about 40° C. and more preferably can operate at a temperature in the range of about 20° C. to about 35° C. The fixed film compartmentalized bioreactors can operate at any suitable pressure, and typically operates at a pressure in the range of about 100 kPa to about 150 kPa, preferably can operate at a pressure in the range of about 100 kPa to about 120 kPa and more preferably can operate at a pressure in the range of about 100 kPa to about 110 kPa.

The effluent is taken at the outlet of the compartmentalized bioreactor in line 110. The effluent in line 110 may comprise sulfides in the range of about 0.1 mg/L to about 0.5 mg/L sulfides and is taken as a purified water stream from the bioreactor. The purified water stream in line 110 may preferably comprise sulfides in the range of about 0.1 mg/L to about 0.2 mg/L sulfides. The sulfide free water taken as final effluent in line 110 from the bioreactor may be used as fracking make-up water for discharge in the case of industrial waste water.

One of the bioreactors (100) may have water following through the vessel and the other bioreactor (200) will be in batch sulfur digestion mode. In the bioreactor with flow, the first chamber of the bioreactor will have reduced aeration (about 0.1 to about 1.0 scfm air/m$^2$ bioreactor surface area) to minimize stripping of hydrogen sulfide. Under these conditions, elemental sulfur will accumulate in the bioreactor by attaching to the highly porous foam packing in the fixed bed bioreactor. When the level of elemental sulfur becomes high enough to bind the bioreactor packing, valves may be switched to redirect flow through the other parallel bioreactor and place this bioreactor in a batch mode. The aeration in the first chamber will increase to a high aeration condition (about 1.0 to about 5.0 scfm air/m$^2$ bioreactor surface area) to facilitate conversion of the accumulated elemental sulfur to sulfuric acid. The pH in the batch bioreactor may be maintained in the range of about pH 2 to about pH 9 by addition of base. The aeration in the first chamber of the other bioreactor will be changed to the low aeration condition to reduce hydrogen sulfide stripping and promote sulfide oxidation to elemental sulfur as shown in FIG. 1. The second stage may be operated in batch mode to digest in-situ elemental sulfur accumulated on the fixed film packing of the compartmentalized bioreactors. The first stage and second stage bioreactor may switch between the flow through and batch mode to digest in-situ the accumulated elemental sulfur to sulfate ion. After a certain period of time, in which all the entrained elemental sulfur in bioreactor 200 has been converted to sulfate ion, the flow to bioreactor 100 will be switched to bioreactor 200 and bioreactor 100 will then operate in batch mode. The two bioreactor systems will thus switch back and forth between flow and batch modes as needed.

The purified effluent stream from the bioreactor in line 110 comprises reduced sulfide concentration to about less than 0.5 mg/L and preferably of about less than 0.2 mg/L. The purified effluent stream may have a pH in the range of about pH 2 to about pH 7. The purified effluent water may be reused in an industrial process or discharged into nearby ground water.

EXAMPLES

The following example is provided to illustrate one or more preferred embodiments of the invention, but are not limited embodiments thereof. Numerous variations can be made to the following example that lies within the scope of the invention.

Example 1

A pilot test of a fixed film (immobilized cell) bioreactor was conducted to treat a sulfidic groundwater with a high concentration of hydrogen sulfide (100-200 mg/L). The first chamber of the bioreactor was operated under a low aeration condition (<1.0 scfm air/m2 bioreactor surface area). The subsequent chambers were operated under high aeration (>1.0 scfm air/m2 bioreactor surface area).

The mass balance of sulfur in the bioreactor during the operational phase of this test showed that the combination of low initial aeration and high subsequent aeration resulted in minimal stripping (<15%) of hydrogen sulfide but a significant amount of accumulation of elemental sulfur in the bioreactor as shown in the following TABLE 1:

TABLE 1

| Fate of Sulfide Input | % Total Sulfur Loaded (sulfide/Thiosulfate)* | | |
|---|---|---|---|
| | Test - 1 | Test - 2 | Test - 3 |
| Stripped H2S, relative to S2— in | 15% | 8% | 13% |
| Converted to SO4, relative to S2— in | 33% | 42% | 29% |
| Accumulated So, relative to S2— in | 72% | 73% | 74% |

*Thiosulfate oxidation contributes to sulfur mass balance >100% from Sulfide

The results show that the majority of the elemental sulfur was trapped by the packing of the bioreactors fixed bed. The ability to trap the elemental sulfur on the packing material mitigates the need to pump sulfur solids from one bioreactor vessel to another. The pumping of wet elemental sulfur solids is very problematic due to their sticky nature and cause frequent plugging of pipes and pumps. Previous attempts to handle these solids and transport between vessels has led to commercial failure of biological systems for sulfide removal from refinery wastewater. The in-situ digestion of elemental sulfur adsorbed to packing material negates the problems with handling wet slurries of elemental sulfur.

Figure 2:
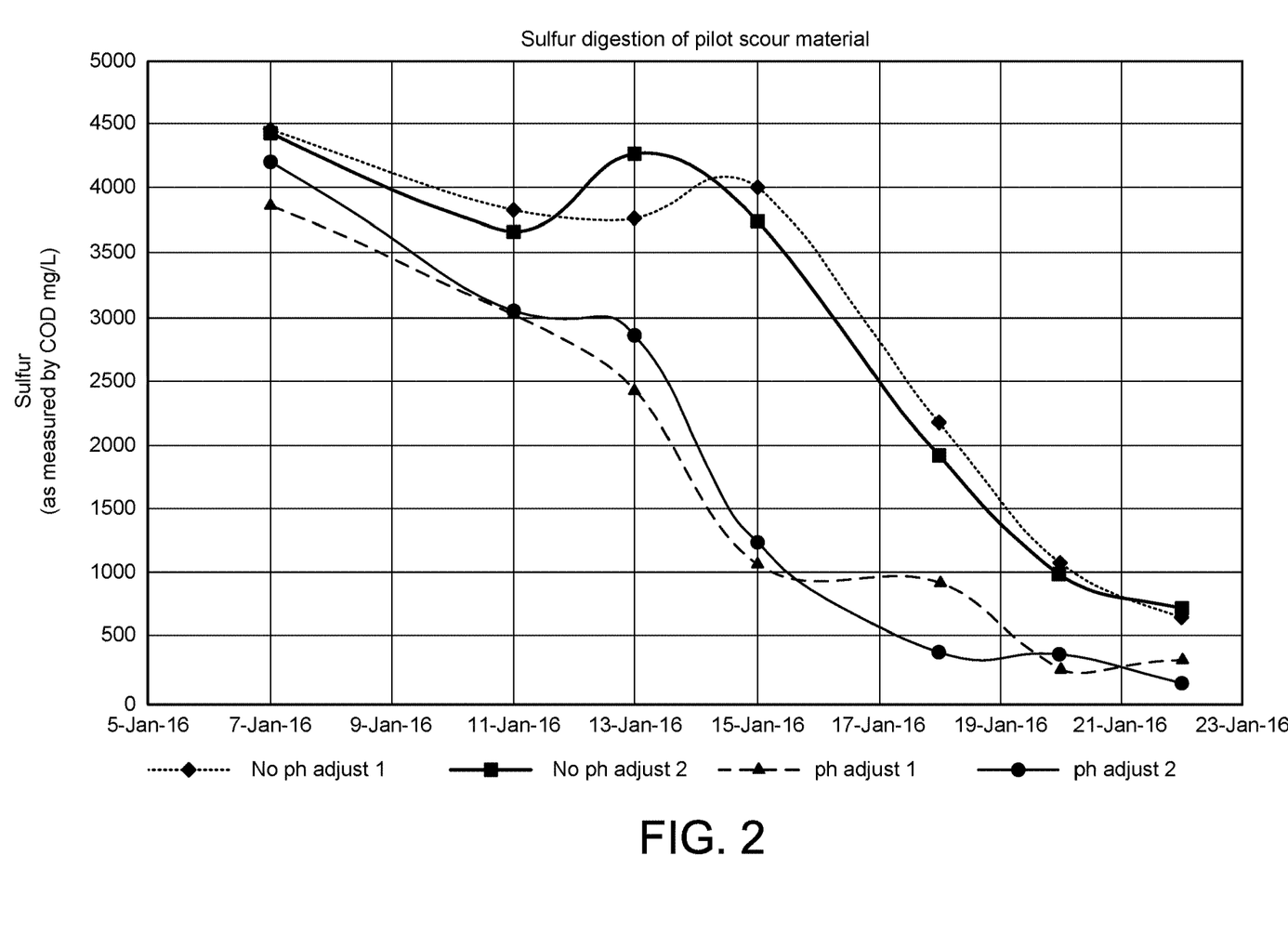
FIG. 2 is an illustration of the degradation of accumulated elemental sulfur.

The digestion of this accumulated elemental sulfur was evaluated in a test flask under pH controlled and uncontrolled conditions as shown in FIG. 2. The degradation of accumulated elemental sulfur was greater than 95%. The digestion of elemental sulfur under high aeration conditions is facilitated by pH adjustment.

While the present invention has been described with what are presently considered the preferred embodiments, it is to be understood that the present invention is not limited to the disclosed embodiments, but it is intended to cover various modifications and equivalent arrangements included within the scope of the appended claims.

Specific Embodiments

While the following is described in conjunction with specific embodiments, it will be understood that this description is intended to illustrate and not limit the scope of the preceding description and the appended claims.

A first embodiment of the invention is a process for biological conversion of hydrogen sulfide in a solution to sulfate ion in a feed water stream using a fixed film compartmentalized bioreactors, comprising passing said water stream through a first stage of the fixed film compartmentalized bioreactor operating under low aeration conditions; oxidizing hydrogen sulfide to elemental sulfur; stripping of hydrogen sulfide from the first stage of the bioreactor; passing the elemental sulfur to a second stage of the fixed film compartmentalized bioreactor operating under high aeration and pH control; oxidizing elemental sulfur to sulfate ion; removing a purified water stream from the second stage comprising sulfides in the range of about 0.1 mg/L to about 0.5 mg/L sulfides from said bioreactor; and wherein an effective quantity of autotrophic obligate chemolithotrophic bacteria is immobilized on a highly porous foam packing material with high surface area within said bioreactor. An embodiment of the invention is one, any or all of prior embodiments in this paragraph up through the first embodiment in this paragraph wherein said water stream is selected from the group consisting of briny ground water, fracking wastewater, sulfidic caustic wastewater, sour water from refining or from petrochemical processing, sulfidic sewer water, and sour water generated by anaerobic digesters and mixtures thereof. An embodiment of the invention is one, any or all of prior embodiments in this paragraph up through the first embodiment in this paragraph wherein autotrophic obligate chemolithotrophic bacteria are selected from the group consisting of *Acidithiobacillus ferrooxidans, Thermithiobacillus tepidarius, Sulfurimonas denitrificans, Desulfocapsa sulfoexigens*, and some species of *Thiobacillus, Halothiobacillus, Acidiphilium, Thiomicrospira, Sulfolobus, Acidianus, Sulfurisphaera*, and *Sulfurococcus*. An embodiment of the invention is one, any or all of prior embodiments in this paragraph up through the first embodiment in this paragraph wherein said purified water stream comprises less than about 0.1 mg/L to about 0.2 mg/L sulfides. An embodiment of the invention is one, any or all of prior embodiments in this paragraph up through the first embodiment in this paragraph further comprising passing the hydrogen sulfide stripped from the first stage to a trickling filter or a bio-filter to convert sulfide to sulfate ion. An embodiment of the invention is one, any or all of prior embodiments in this paragraph up through the first embodiment in this paragraph wherein the ratio of air to sulfide in the trickling bio-filter is about 0.5 Liters of air/mg of sulfide to about 4 liters of air/mg of sulfide. An embodiment of the invention is one, any or all of prior embodiments in this paragraph up through the first embodiment in this paragraph wherein the compartmentalized bioreactors are operated in parallel. An embodiment of the invention is one, any or all of prior embodiments in this paragraph up through the first embodiment in this paragraph wherein the second stage may be operated in batch mode to digest in-situ elemental sulfur accumulated on the fixed film packing of the said bioreactor. An embodiment of the invention is one, any or all of prior embodiments in this paragraph up through the first embodiment in this paragraph wherein the first stage and second stage bioreactor may switch between the flow through and batch mode to digest in-situ the accumulated elemental sulfur to sulfate ion. An embodiment of the invention is one, any or all of prior embodiments in this paragraph up through the first embodiment in this paragraph wherein a majority of sulfides within said mixed water stream are oxidized to sulfates by said chemolithotrophic sulfur oxidizing bacteria. An embodiment of the invention is one, any or all of prior embodiments in this paragraph up through the first embodiment in this paragraph wherein each of compartmentalized bioreactor comprises three chambers. An embodiment of the invention is one, any or all of prior embodiments in this paragraph up through the first embodiment in this paragraph wherein said mixed water stream flow through said autotrophic obligate chemolithotrophic bacteria. An embodiment of the invention is one, any or all of prior embodiments in this paragraph up through the first embodiment in this paragraph wherein said packing material contains about 4,000 mg/L to about 12,000 mg/L of fixed biomass. An embodiment of the invention is one, any or all of prior embodiments in this paragraph up through the first embodiment in this paragraph wherein the amount of air in the first stage is about 0.1 scfm air/m$^2$ to about 1.0 scfm air/m$^2$ bioreactor surface area and pH is about 2 to about 9. An embodiment of the invention is one, any or all of prior embodiments in this paragraph up through the first embodiment in this paragraph wherein the amount of air in the second stage is about 1.0 scfm air/m$^2$ to about 5.0 scfm air/m$^2$ bioreactor surface area and pH is about 2 to about 9. An embodiment of the invention is one, any or all of prior embodiments in this paragraph up through the first embodiment in this paragraph further comprising controlling the pH in the range of about 2 to about 9 by adding a base such as sodium hydroxide or sodium carbonate. An embodiment of the invention is one, any or all of prior embodiments in this paragraph up through the first embodiment in this paragraph wherein the temperature of the fixed film compartmentalized bioreactors is about 10° C. to about 65° C. and the pressure of the fixed film compartmentalized bioreactors is about 100 kPa to about 150 kPa. An embodiment of the invention is one, any or all of prior embodiments in this paragraph up through the first embodiment in this paragraph further comprising trapping the elemental sulfur in the high porosity foam packing in the first stage. An embodiment of the invention is one, any or all of prior embodiments in this paragraph up through the first embodiment in this paragraph further comprising oxidizing the stripped sulfide to sulfuric acid in a tickling bio-filter or bio-filter type or with a sulfide adsorbent or oxidant. An embodiment of the invention is one, any or all of prior embodiments in this paragraph up through the first embodiment in this paragraph wherein the said purified water stream has a pH of between pH 2 and pH 7.

Without further elaboration, it is believed that using the preceding description that one skilled in the art can utilize the present invention to its fullest extent and easily ascertain the essential characteristics of this invention, without departing from the spirit and scope thereof to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

The invention claimed is:

1. A process for biological conversion of hydrogen sulfide in a solution to sulfate ion in a feed water stream using a fixed film compartmentalized bioreactor, comprising:
    a) passing said feed water stream through a first stage of the fixed film compartmentalized bioreactor operating under low aeration conditions;
    b) oxidizing hydrogen sulfide to elemental sulfur;
    c) stripping of hydrogen sulfide from the first stage of the bioreactor;
    oxidizing the elemental sulfur to sulfate ion in a second stage of the fixed film compartmentalized bioreactor operating under high aeration and pH control;
    e) removing a purified water stream from the second stage comprising sulfides in the range of about 0.1 mg/L to about 0.5 mg/L sulfides from said bioreactor; and
    f) wherein an effective quantity of autotrophic obligate chemolithotrophic bacteria is immobilized on a highly porous foam packing material with high surface area within said bioreactor.

2. The process of claim 1 wherein said feed water stream is selected from the group consisting of briny ground water, fracking wastewater, sulfidic caustic wastewater, sour water from refining or from petrochemical processing, sulfidic sewer water, and sour water generated by anaerobic digesters and mixtures thereof.

3. The process of claim 1 wherein said autotrophic obligate chemolithotrophic bacteria are selected from the group consisting of *Acidithiobacillus ferrooxidans, Thermithiobacillus tepidarius, Sulfurimonas denitrificans, Desulfocapsa sulfoexigens, Thiobacillus, Halothiobacillus, Acidiphilium, Thiomicrospira, Sulfolobus, Acidianus, Sulfurisphaera,* and *Sulfurococcus.*

4. The process of claim 1 wherein said purified water stream comprises between about 0.1 mg/L to about 0.2 mg/L sulfides.

5. The process of claim 1 further comprising passing the hydrogen sulfide stripped from the first stage to a trickling filter or a bio-filter to convert sulfide to sulfate ion.

6. The process of claim 5 wherein the hydrogen sulfide is passed to a trickling filter and wherein the ratio of air to sulfide in the trickling filter is about 0.5 Liters of air/mg of sulfide to about 4 liters of air/mg of sulfide.

7. The process of claim 1 wherein the compartmentalized bioreactors are operated in parallel.

8. The process of claim 1 wherein the second stage is operated in batch mode to digest in-situ elemental sulfur accumulated on the fixed film packing of the said bioreactor.

9. The process of claim 1 wherein the first stage and second stage bioreactor are configured to switch between the flow through and batch mode to digest in-situ the accumulated elemental sulfur to sulfatetion.

10. The process of claim 1 wherein a majority of sulfides within said mixed water stream are oxidized to sulfates by said chemolithotrophic sulfur oxidizing bacteria.

11. The process of claim 7 wherein the compartmentalized bioreactor comprises three chambers.

12. The process of claim 1 wherein said feed water stream flow through said autotrophic obligate chemolithotrophic bacteria.

13. The process of claim 1 wherein said packing material contains about 4,000 mg/L to about 12,000 mg/L of fixed biomass.

14. The process of claim 1 wherein the amount of air in the first stage is about 0.1 scfm air/m2 to about 1.0 scfm air/m2 bioreactor surface area and pH is about pH 2 to about pH 9.

15. The process of claim 1 wherein the amount of air in the second stage is about 1.0 scfm air/m2 to about 5.0 scfm air/m2 bioreactor surface area and pH is about pH 2 to about pH 9.

16. The process of claim 14 further comprising controlling the pH in the range of about 2 to about 9 by adding a base.

17. The process of claim 1 wherein the temperature of the fixed film compartmentalized bioreactors is about 10° C. to about 65° C. and the pressure of the fixed film compartmentalized bioreactors is about 100 kPa to about 150 kPa.

18. The process of claim 1 further comprising trapping the elemental sulfur in the high porosity foam packing in the first stage.

19. The process of claim 1 further comprising oxidizing the stripped sulfide to sulfuric acid in a trickling filter or bio-filter or with a sulfide adsorbent or oxidant.

20. The process of claim 1 wherein the said purified water stream has a pH of between pH 2 and pH 7.

* * * * *